(12) United States Patent
Baumgarten et al.

(10) Patent No.: US 6,512,007 B1
(45) Date of Patent: Jan. 28, 2003

(54) **USE OF *GALIELLA LACTONE***

(75) Inventors: Jörg Baumgarten, Wuppertal; Marcus Weidler, Odenthal; Gerhard Erkel, Kaiserslautern; Heidrun Anke, Kaiserslautern; Timm Anke, Kaiserslautern, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/895,685

(22) Filed: Jun. 29, 2001

(30) Foreign Application Priority Data

Jul. 3, 2000 (DE) .......................................... 100 32 242
Sep. 25, 2000 (DE) .......................................... 100 47 295

(51) Int. Cl.$^7$ .............................................. A61K 31/35
(52) U.S. Cl. ...................................................... 514/460
(58) Field of Search ......................................... 514/460

(56) References Cited

FOREIGN PATENT DOCUMENTS

WO   WO 99/36417   7/1999

OTHER PUBLICATIONS

Kushner, "Regulation of the Acute Phase Response by Cytokines", *Perspectives in Biology and Medicine* 36, 4: 611–612 (1993).

Gabay et al., "Acute–Phase Proteins and Other Systemic Responses to Inflammation", *The New England Journal of Medicine*, 448–454 (Feb. 11, 1999).

Gauldie et al., "Interferon $\beta_2$/B–cell stimulatory factor type 2 shares identity with monocyte–derived hepatocyte–stimulating factor and regulates the major acute phase protein response in liver cells", *Proc. Natl. Acad. Sci. USA*, vol. 84: 7251–7255 (Oct. 1987).

Darnell Jr. et al., "Jak–STAT Pathways and Transcripitonal Activation in Response to IFNs and Other Extracellular Signaling Proteins", *Science*, vol. 264: (Jun. 3, 1994).

Darnell Jr., "STATs and Gene Regulation", *Science*, vol. 277: (Sep. 12, 1997).

Heinrich et al., "Interleukin–6–type cytokine signalling through the gp130/Jak/STAT pathway", *Biochem. J.* 334: 297–314 (1998).

Hautzel et al., "Screening of Basidiomycetes and Ascomycetes for Plant Growth Regulating Substances. Introduction of the Gibberellic Acid Induced de–novo Synthesis of Hydrolytic Enzymes in Embryoless Seeds in Triticum aestivum as Test System", *Z. Naturforsch.* 45c: 1093–1098 (1990).

Lincoff et al., "The Audubon Society Field Guide to North American Mushrooms", Alfred A. Knopf, New York (1981).

Morley et al., "Serum C–Reactive Protein Levels in Disease", *Ann. N.Y. Acad. Sci.* 389: 406–418 (1982).

Deviere et al., "Immunoglobulin A and Interleukin 6 Form a Positive Secretory Feedback Loop: A Study of Normal Subjects and Alcoholic Cirrhotics", *Gastroenterology* 103: 1296–1301 (1992).

Rosenbloom et al., "Leukocyte Activation in the Peripheral Blood of Patients With Cirrhosis of the Liver and SIRS", *JAMA*, vol. 274, No. 1: 58–65 (Jul. 5, 1995).

Cressman et al., "Liver Failure and Defective Hepatocyte Regeneration in Interleukin–6–Deficient Mice", *Science*, vol. 274: 1379–1383 (Nov. 22, 1996).

Stein et al., "IL–6 as a drug discovery target", *Drug Discovery Today*, vol. 3, No. 5: 202–213 (May 1998).

Hirano et al., "Roles of STAT3 in mediating the cell growth, differentiation and survival signals relayed through the IL–6 family of cytokine receptors", *Oncogene* 19: 2548–2556 (2000).

Ni et al., "Inhibition of Constitutively Activated Stat3 Signaling Pathway Suppresses Growth of Prostate Cancer Cells", *Cancer Research* 60: 1225–1228 (Mar. 1, 2000).

Page et al., "Elevated phosphorylation of AKT and Stat3 in prostate, breast, and cervical cancer cells", *International Journal of Oncology* 17: 23–28 (2000).

Grant et al., "The oncostatin M signalling pathway: reversing the neoplastic phenotype?", *Molecular Medicine Today* vol. 5: 406–412 (Sep. 1999).

Erkel et al., "Inhibition of NF–kB Activation by Panepoxydone", *Biochemical And Biophysical Research Communications* 226: 214–221 (1996).

Seidel et al., "Spacing of palindromic half sites as a determinant of selective STAT (signal transducers and activators of transcription) DNA binding and transcriptional activity", *Proc. Natl. Acad. Sci. USA*, vol. 92: 3041–3045 (Mar. 1995).

Weidler et al., "Inhibition of interleuken–6 signaling by galiellalactone", FEBS Letters 484 (2000) 1–6.

*Primary Examiner*—Raymond Henley, III
(74) *Attorney, Agent, or Firm*—Connolly Bove Lodge & Hutz LLP

(57) ABSTRACT

The invention relates to the use of the substance known under the name of *galiella lactone* as pharmaceutical, in particular for the treatment of inflammatory processes.

5 Claims, 5 Drawing Sheets

SEQUENCE LISTING

```
<160> NUMBER OF SEQ ID NOS: 4

<210> SEQ ID NO 1
<211> LENGTH: 21
<212> TYPE: DNA
<213> ORGANISM: Unknown Organism
<220> FEATURE:
<223> OTHER INFORMATION: Description of Unknown Organism:
      double-stranded oligonucleotide

<400> SEQUENCE: 1
ctagcgattt ccccgaaatg g                                      21

<210> SEQ ID NO 2
<211> LENGTH: 21
<212> TYPE: DNA
<213> ORGANISM: Unknown Organism
<220> FEATURE:
<223> OTHER INFORMATION: Description of Unknown Organism:
      double-stranded oligonucleotide

<400> SEQUENCE: 2
ctagccattt cggggaaatc g                                      21
```

-continued

```
<210> SEQ ID NO 3
<211> LENGTH: 19
<212> TYPE: DNA
<213> ORGANISM: Unknown Organism
<220> FEATURE:
<223> OTHER INFORMATION: Description of Unknown Organism:
      double-stranded oligonucleotide

<400> SEQUENCE: 3
gatccatttc ccgtaaatc                                            19

<210> SEQ ID NO 4
<211> LENGTH: 19
<212> TYPE: DNA
<213> ORGANISM: Unknown Organism
<220> FEATURE:
<223> OTHER INFORMATION: Description of Unknown Organism:
      double-stranded oligonucleotide

<400> SEQUENCE: 4
gatttacggg aaatggatc                                            19
```

USE OF GALIELLA LACTONE

Figure 1:
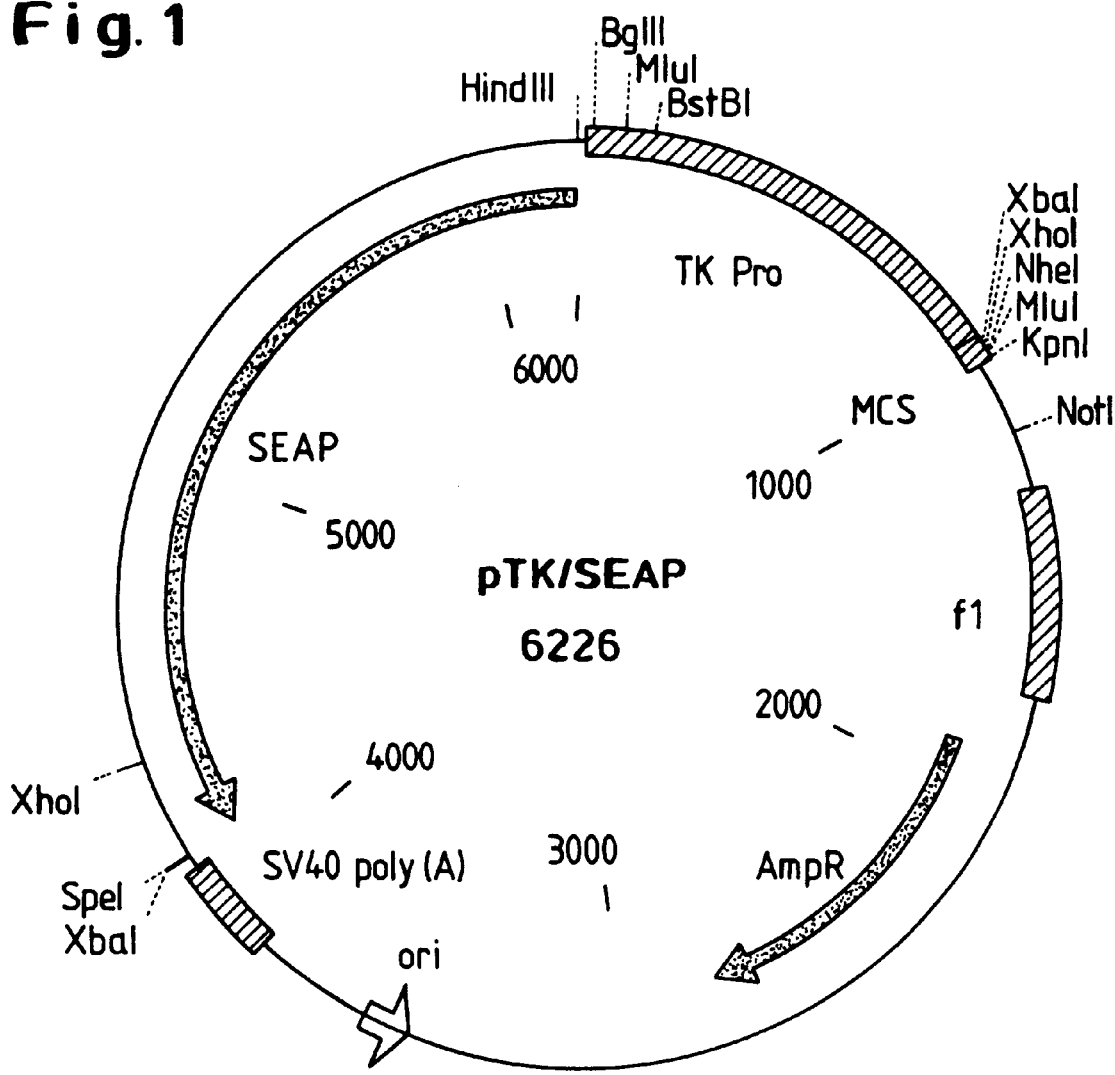
Figure 2:
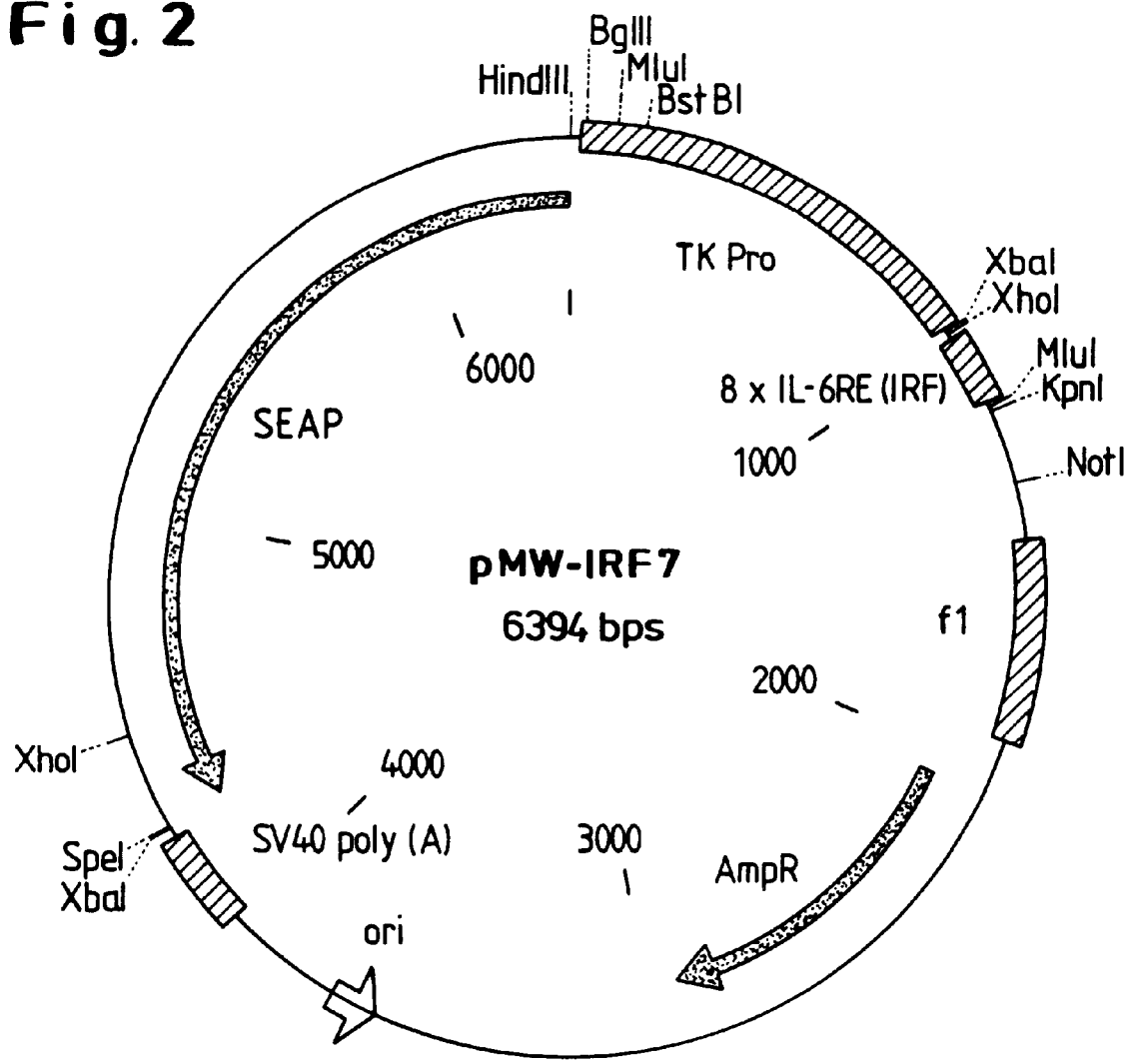

The invention relates to the use of the substance known under the name of *galiella lactone* as pharmaceutical, in particular for the treatment of inflammatory processes.

Inflammations are distinguished by a large number of changes even in organ systems which are not in the immediate vicinity of the site of the inflammation. All the systemic changes associated with an inflammation are embraced by the term "acute phase response". This also applies to chronic inflammatory phenomena (*Perspect. Biol. Med.*, 1993, 36: 611–22). The principal part is played in the development of acute phase response by the altered rate of synthesis of so-called acute phase proteins (AP proteins) in the liver (*N. Engl. J. Med.*, 1999, 340: 448–54). The acute phase response occurs in infections, traumats, operations, burns, organ damage and advanced stages of malignant diseases. The main mediator of the acute phase response is interleukin-6 (IL-6) (*Proc. Natl. Acad. Sci. USA*, 1987, 84: 7251–5).

IL-6 uses tyrosine kinases from the Janus Kinase (Jak) family and transcription factors from the signal transducer and acovator of transcription (Stat) family as the main mediators of intracellular signal transduction. IL-6 induces phosphorylation and thus activation of the transcription factors Stat3 and Stat1 (to a smaller extent) (*Science*, 1994, 264: 1415–21: *Science*, 1997, 277: 1630–5). After the activation. Stat3 and Stat1 are translocated into the cell nucleus and, after binding to their binding sites on the DNA, cause expression of the genes of AP proteins therein (*Biochem. J.*, 1998, 334: 297–314).

Treatments of inflammatory processes corresponding to the current state of the art, for example with corticosteriods, are not without unwanted side effects. There is a need for therapeutic agents which reduce or suppress the unwanted or unwantedly strong expression of the IL-6 -induced AP proteins in the diseases mentioned above and below without at the same time intervening elsewhere in cellular metabolism. For this reason, Stat3 is regarded as a suitable target for developing novel active substances against a non-beneficial, excessive (not self-limiting) acute phase response as is present, for example, in the case of cirrhosis of the liver.

It has now been found, surprisingly, that the compound of the formula (I).

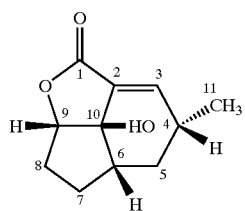

(I)

which is called *galiella lactone* is outstandingly suitable for the treatment of inflammatory processes induced by excessive expression of the IL-6-induced acute phase proteins. In this connection, the substance has a specific effect on IL-6 signal induction which has not previously been disclosed for any substance.

*Galiella lactone* of the formula (I) is disclosed in *Z. Naturforsch.* 1990, 45 c; 1093–8 (and the thesis by R. Hautzel, University of Kaiserslautem 1989) and can be isolated from the fungus *Galiella rufa* (subdivision *Ascomycotina*, class *Discomycotina*, order *Pezizales*, family *Sarcosomaraceae*, genus *Galiella*) as described therein or in the thesis by H. J. Knerr, University of Kaiserslaurem 1995. No report of its use as pharmaceutical has appeared to date. *Galiella rufa* is described, for example, in: Gary H. Lincoff, Carol Nehring, *The Audubon Society Field Guide to North American Mushrooms*, Alfred A. Knopf, N.Y. 1981.

*Galiella lactone* has the physical and chemical properties described hereinafter. *Galiella lactone* forms white crystals which are readily soluble in polar solvents (methanol, pyridine, ethyl acetaze, acetonitrile, tert-butyl methyl ether (lMBE), tetrahydrofurn (THF) and water) and scarcely soluble in nonpolar solvents (cyclohexane, n-pentane, n-hexane). It was possible with the aid of the mass spectra (Table 1) to establish firstly the molecular weight of 194 Da and then the molecular formula of $C_{11}H_{14}O_3$.

TABLE 1

Relative frequency of the peaks in the mass spectra of galiella lactone. APCI (positive polantry, fragmenter voltage: 70 V, vaporizer temperature: 400° C.);

| CI | | APCI | |
|---|---|---|---|
| m/z | Intensity [%] | m/z | Intensity [%] |
| 194.8 (MH$^+$) | 100 | 195.1 (MH$^+$) | 69 |
| 177.0 | 70 | 177.1 | 100 |
| 159.2 | 19 | 159.1 | 13 |
| 149.2 | 47 | 149.1 | 17 |
| 131.4 | 27 | 133.1 | 16 |
| 105.5 | 12 | 131.1 | 15 |

TABLE 2

$^1$H (500 MHz) (δ/ppm; multiplicity) and $^{13}$C (125 MHz) (δ/ppm) NMR data for galiella lactone in CDCl$_3$. The CHCl$_3$/CDCl$_3$ signal was used as reference).

| H/C No. | $^1$H data | $^{13}$C data |
|---|---|---|
| 1 | — | 170.4 |
| 2 | — | 130.6 |
| 3 | 6.85; d | 149.6 |
| 4 | 2.53; m | 28.6 |
| 5 | 0.90; m; 2.13; m | 32.7 |
| 6 | 2.32; m | 42.7 |
| 7 | 1.02; m; 1.71; m | 31.0 |
| 8 | 1.60; m; 1.95; m | 31.0 |
| 9 | 4.64; m | 90.0 |
| 10 | — | 81.3 |
| 11 | 1.05; m | 20.5 |

The structure was elucidated by means of two-dimensional homonuclear and heteronuclear NMR spectroscopy ($^1$H and $^{13}$C). The assignment of the NMR signals to the respective nuclei can be found in Table 2. The UV spectrum of *galiella lactone* shows a maximum at 219 nm. The characteristic peaks in the IR spectrum and their assignment can be found in Table 3.

TABLE 3

Assignment of characteristics peaks in the IR spectrum of galiella lactone to functional groups.

| $\bar{v}$ of peak [cm$^{-1}$] | Assignment |
|---|---|
| 3435 | tert-alcohol (—OH stretching vibration) |
| 2961-2933 | =CH stretching vibration |

TABLE 3-continued

Assignment of characteristics peaks in the IR spectrum of galiella lactone to functional groups.

| $\overline{v}$ of peak [cm$^{-1}$] | Assignment |
|---|---|
| 1742 | aliphatic ester (C=O stretching vibration) |
| 1670 | C=C stretching vibration |
| 1460 | —CH$_3$ and CH$_2$ deformation vibration |

The invention also relates to pharmacologically active derivatives of *galiella lactone* and their use analogous to *galiella lactone*.

In the 1930s, the inflammatory phenomena leading to changes in organ systems were investigated in detail for the first time. This led to the discovery of C-reactive protein (so-called because it reacts with the C polysaccharide of pneumococci) in the plasma of patients during the acute phase of pneumonia induced by pneumococci. Since then, all systemic changes associated with an inflammation are summarized by the term "acute phase response", and this also applies to chronic inflammatory phenomena.

TABLE 4

Human AP proteins (N. Engl. J. Med. 1999, 340; 448–54)

Proteins whose plasma concentrations increase:
Complement system: C3, C4, C9, factor B, Cl inhibitor, C4b building protein, mannose binding lectin
Coagulation and fibrinolytic system: fibrinogen, plasminogen, tissue plasminogen activator, urokinase, protein S, vitronectin, plasminogen activator inhibitor 1
Antiproteases: $\alpha_1$-protease inhibitor, $\alpha_1$-antichymotrypsin, pancreatic secretory trypsin inhibitor, inter-$\alpha$-trypsin inhibitors
Transport proteins: ceruloplasmin, haptoglobin, hemopexin
Inflammatory system: secreted phospholipase A$_2$, lipopolysaccharide binding protein. IL-1 receptor antagonist, granulocyte-colony stimulating factor
Others: C-reative protein, serum amyloid A, $\alpha_1$-acid glycoprotein, fibronectin, ferritin, angiotensinogen
Proteins whose plasma concentrations decrease:
albumin, transferrin, $\alpha_2$-HS glycoprotein, $\alpha$-fetoprotein, thyroxine binding globulin, insulin like growth factor I, factor XII A rather arbitrary distinction is made between two aspects of the acute phase response: thus, on the one hand, changes in concentration of many proteins in the plasma, the so-called acute phase proteins (AP proteins), are observed (Table 4) and, on the other hand, changes occur in the behaviour and general physiological state (see Table 5). The latter are, of course, caused by the former. A protein is included by definition in the group of AP proteins if, during inflammatory disorders, its plasma concentration increases (positive AP proteins) or decreases (negative AP proteins) by at least 25% (ef., for example, *Ann. N.Y. Acad. Sci.* 1982, 389: 406–18). The changes in concentrations of the AP proteins derive principally from their altered rate of synthesis in the liver.

TABLE 5

Phenomena occuring in the acute phase

Neuroendocrine changes: fever, insomnia, anorexia, increased secretion of the following hormones: corticotropin-releasing hormone, corticotropin, cortisol, vasopressin and catecholamines
Changes in haemasopoiesis; anaemia, leukocytosis, thrombocytosis
Metabolic changes: muscle atrophy and negative nitrogen balance reduced gluconeogenesis, osteoporosis, increased hepatic lipogenesis, increased lipolysis in adipose tissue, reduced lipoprotein lipase

TABLE 5-continued

Phenomena occuring in the acute phase activity in muscle and adipose tissue, cachexia
Changes in the liver: increased fibrinogen production leading to cirrhosis of the liver, increased production of metallothionein and manganese superoxide dismutase
Others: hypozincaemia, hypoferraemia, hypercupraemia, secondary amyloidosis The level of induction of the individual proteins varies widely. Thus, the plasma level of ceruloplasmin increases by just 50%, whereas that of C-reactive protein increases by a factor of 1000.

The pharmacological effect of inhibitors of the signal transducer and activator of transcription 3 and thus of IL-6-dependent gene expression Signal transducer and activator of transcription 3 (Stat3) assumes a special role in the control of the expression of genes having in their promoter sequence an IL-6 responsive element of class II (IL-6RE IL, synonymous with acute phase responsive element, APRE) (5'-TTNNNNAA-3' or 5'-TTNNNNNAA-3'). To this extent, Stat3 is a transcription factor. However, the physiological activity of Stat3 in the control of gene expression is subject to the following principle of regulation:

binding of IL-6 to a receptor complex consisting of the IL-6 receptor and two gp130 molecules results in activation of the gp130-associated kinases Jak1, Jak2 and Tyk2. These initially phosphorylate tyrosine residues in the cytoplasmic part of gp130, which thus become binding sites for SH2 domains of Stat1 and Stat3. After the Stats have bound, they are phosphorylated by the Jaks at specific tyrosine residues and subsequently form homodimers or heterodimers. The activated dimers are translocated into the core, bind to IL-6RE II there are subsequently induce the transcription of the targets genes. On their way into the cell nucleus or in the cell nucleus, the dimers are also phosphorylated on specific serine residues by an as yet unknown serine kinase (*Biochem. J.*, 1998, 334: 297–314).

A crucial feature of Stat3 compared with other transcription factors is that Stat3 is a primary transcription factor. Primary transcription factors are already present in the cell in inactive form and are activated by an appropriate stimulus in order to be able to display their effect very rapidly. Primary transcription factors are not formed only on activation of the relevant gene and subsequent transcription and translation.

Since the abovementioned gp130-associated kinases Jak1, Jak2 and Tyk2 are also involved in other intracellular signal transduction pathways which, because of the unwanted effects resulting therefrom, are not to be inhibited, they do not represent suitable targets for selective inhibition of the Stat3-mediated gene expression. By contrast, a chemical compound which selectively prevents the binding of Stat3 to its DNA binding sites (IL-6RE II, see above) ought to be useful as pharmaceutical for suppressing Stat3- and thus also IL-6-mediated disease processes.

Stat3 is able primarily to promote all pathophysiological processes involving genes having the Stat3 binding sequence (IL-6RE II) in their promoter. These are specifically genes which play a crucial causative part in immunological complications, in inflammatory diseases, septic shock degenerative diseases such as secondary amyloidosis or else chronic inflammatory diseases such as cirrhosis of the liver. Tab. 5 summarizes the changes occurring when Stat3 activity is increased.

The acute phase response occurs in association with infections, traumata, operations, burns, organ damage and advanced stages of malignant diseases.

The main mediator of the acute phase response is interleukin-6 (IL-6). IL-6 additionally influences a large number of physiological processes. Examples which may be mentioned are bone metabolism, haematopoiesis, immune response, inflammatory processes, development of nerve cells, and cellular proliferation. However, the role of IL-6 in the development of cirrhosis of the liver is of crucial importance (*Gastroenterology* 1994, 107: 789–98). In patients with cirrhosis of the liver there is found to be a positive correlation between the IL-6 plasma level and the organ failure, and the increased secretion of IgA and IgG by peripheral monocytes (*Gastroenterology* 1992, 103: 1296–301: *Jama* 1995; 274: 58–65). It has additionally been possible to show the IL-6 induces the expression of fibrinogen in the liver (*Science* 1996, 274: 1379–83). It is assumed that these changes play a central part in the development of fibrous tissue in the diseased liver, which eventually leads to cirrhosis of the liver (*Drug Discovery Today* 1998, 3: 202–13).

The effect according to the invention of *galiella lactone* is based on the specific inhibition of IL-6 signal induction. *Galiella lactone* is therefore generally suitable for the prophylaxis and/or treatment of inflammatory processes and their sequelae.

Stat3 is likewise an essential factor in the regulation of cell growth, the survival of cells and in cell differentiation (*Oncogene* 2000, 19: 2548–2556) It was possible to show that, for example in rat tumours and human prostate tumours, Stat3 is constitutively activated and that this activation correlates with the malignant potential of the tumours (*Cancer Research* 2000, 60: 1225–1228). Inhibition of Stat3 inhibits the growth of prostate tumour cells significantly. These results show that activation of Stat3 is essential for the progression of prostate tumour cells and that inhibition thereof has a great therapeutic potential for treating prostate tumours.

The importance of the activation of Stat3 has also been described for other types of tumours, for example for the tumours summarized by the term head and neck cancer, for breast cancer and uterine cancer (*International Journal of Oncology* 2000, 17: 23–28), and melanomas (skin cancer), tumours on the ovary, gliomas (brain tumours) and lung tumours (*Molecular Medicine Today* 1999, 5: 406–412).

Besides its well-described function as mediator of the acute phase response, IL-6 has also been described as an important regulator of cellular functions in the nervous system. Several studies have shown that IL-6 is involved both in physiological and in pathophysiological processes within the central nervous system (CNS) (*Molecular Neurobiology* 1997, 15: 307–339).

In the adult CNS (parenchyma and cerebrospinal fluid), the IL-6 levels are low or are below the detection limit. Significantly increased IL-6 levels occur, however, as a common feature of CNS injuries, inflammations and diseases. Increased IL-6 levels have been found, for example, in brain homogenates or cerebrospinal fluid in animal models of multiple sclerosis (*European Journal of Immunology* 1990, 20: 233–235) and multiple sclerosis patients (*Cytokine* 1993, 5: 583–588), in animal models of Parkinsons's disease (*Clinical and Experimental Pharmacology and Physiology* 1999, 26: 680–683) and Parkinson patients (*Advances in Neurology* 1999, 80: 135–139), in patients suffering from Alzheimer's disease (*Acta Neuropathologica* 1995, 89: 544–551), in animal models of neuropathic pain (*Molecular Brain Research* 1998, 62: 228–235), and in various types of CNS infections (for example *Clinical and Experimental Immunology* 1998, 71: 320–323). The main sources of IL-6 under these conditions appear to be astrocytes, microglia, neurons and, in some cases, immigrating immune cells (*American Journal of Physiology* 1992, 263: C1–C16).

Relatively little is known about the effects of IL-6 within the CNS, although it has been assumed that it might have protective functions. This theory derives essentially from in vitro observations indicating a survival- and differentiation-promoting effect of IL-6 on various types of cells in CNS. Studies on transgenic animals with IL-6 expression in the CNS suggest, however, that dysregulation of IL-6 production contributes to the neutropathology and pathophysiology of many CNS disorders. Two different approaches have been taken for overexpression of IL-6 selectively in the CNS: expression of human IL-6 in CNS neurons under the control of the promoter for rat neuron-specific enolase (NSE-IL-6 mice) (*European Journal of Neuroscience* 1995, 7: 2442–2449) and expression of murine IL-6 in astrocytes under the control of the murine GFAP promoter (GFAP-IL6 mice) (*Proceedings of the Natural Academy of Sciences, USA* 1993, 90: 10061–10065). In the NSE-IL6 model, reactive gliosis was found throughout the brain, but this was not associated with a general pathology of neuronal cell populations, of the CNS vascular system or changes in behaviour. In contrast to this, severe neuronal and vascular pathologies, in addition to reactive gliotic processes, have been described in GFAP-IL6 mice. Thus, GFAP-IL-b 6 mice show distinct signs of neurodegeneration, inflammatory processes in the brain, disturbances of blood-brain barrier function and altered electroencephalographic activity. These changes are associated with marked learning deficits and a number of motor disturbances such as disturbed motor coordination, ataxia and tremor.

*Galiella lactone* is particularly suitable for the prophylaxis and treatment of fibrotic disorders of the liver and other organs, cerebrovascular disorders such as, for example, stroke, traumatic injuries to the brain or spinal cord and their sequelae, autoimmune diseases affecting the CNS or PNS, such as, for example, multiple sclerosis, peripheral autoimmune neuropathies, chronic neurodegenerative disorders such as, for example, Alzheimer's disease, Parkinson's disease, psychological disorders such as, for example, depression, anxiety, psychoses, peripheral neuropathies of varying cause such as, for example, diabetic neuropathy, pain caused both central and peripheral pathophysiological mechanisms, cardivascular disorders such as coronary heart disease, arteriosclerosis and restenosis, inflammatory disorders of the gastrointestinal tract such as Crohn's disease (regional enteritis), amyloidoses such as rheumatoid arthritis and Stat3-dependent tumours such as head and neck cancer, breast cancer, uterine cancer and prostate cancer and melanomas, ovarian tumours, gliomas, carcinomas of the lung, and cachexia-inducing tumours.

The present invention also includes pharmaceutical preparations which, besides inert, nontoxic, pharmaceutically suitable excipients and carrier, contain *galiella lactone*, or which consist of *galiella lactone,* and processes for producing these preparations.

*Galiella lactone* should be present in these preparation in a concentration of 0.1 to 99.5% by weight, preferably of 0.5 to 95% by weight, of the complete mixture.

Besides *galiella lactone,* the pharmaceutical preparations may also contain other pharmaceutical active substances.

The abovementioned pharmaceutical preparations can be produced in a conventional way by known methods, for example with the excipient(s) or carrier(s).

*Galiella lactone* should normally be administered in total amounts of about 0.01 to about 100 mg/kg, preferably in total amounts of about 1 mg/kg to 50 mg/kg, of body weight every 24 hours, where appropriate in the form of several individual doses, to achieve the desired result.

However, it may be advantageous where appropriate to deviate from the stated amounts, specifically depending on the nature and body weight of the subject treated, on the individual behaviour toward the medicament, on the nature and severity of the disorder, the type of preparation and administration, and the time or interval over which administration takes place.

The effect is demonstrated by means of the following examples without any restriction being inferable therefrom.

EXAMPLES

Example A

Inhibition of IL-6-mediated gene in human liver carcinoma cells

The following bioassay was carried out for fundamental exemplary experiments for detecting the inhibition of IL-6- and Stat3-mediated gene expression:

The initial vector used was the vector pTK/SEAP (*Biochem. Biophys. Res. Commun.,* 1996, 226: 214–21) (see FIG. 1) which contains the gene of secreted alkaline phosphatase (SEAP) as reporter gene. This vector was linearized with the restriction enzyme NheI and then dephosphorylated. The following oligonucleotides

5'-CTAGCGATTTCCCCGAAATGG-3' SEQ ID NO:1

3'-GCTAAAGGGGCTTTACCGATC-5' SEQ ID NO:2 which contain a binding site for Stat3 and Stat1 proteins (cf. *Proc. Natl. Acad. Sci. USA,* 1995, 92: 3041–5) were phosphorylated, ligated and precipitated with ethanol. The characteristic concatemer ladder was checked by polyacrylamide gel electrophoresis (PAGE).

The linearized vector was ligated to the concatemers. The vector which contained 8 consecutively inserted copies of the oligonucleotides depicted above the Stat3/1 recognition sequence was selected (see FIG. 3). This results in expression of SEAP in the recombinant plasmid produced in this way being regulated by the Stat3/1 binding sites. This expression construct was subjected to DNA sequencing for analysis and transfected into the human liver carcinoma cell line HepG2 (*American Type Culture Collection,* 12301 Parklane Drive, Rockville, Md. 20852, USA)

Assay procedure:

The HepG2 cells were cultivated in a moist atmosphere with 5% $CO_2$ at 37° C. in 50 ml of DMEM (*Gibco BRL, Life Technologies GmbH. Dieselstr,* 5, 76344 Eggenstein) with 10% fetal calf serum, and penicillin/streptomycin (100 iu) in 600 ml cell culture bottles. The medium was renewed 24 h before starting the experiment. On the day of the experiment, the cells were detached by treatment with trypsin and centrifuged at 1000 ×g and 4° C. The supernatant was decanted off and the cell pellet was resuspended in 0.2 ml of cold Hebs buffer (20 mM HEPES, 137 mM NaCl, 5 mM KCl, 0.7 mM $Na_2HPO_4$, 6 mM dextrose, pH 7.05). The cell count was determined using a counting chamber and was adjusted to 6–8×$10^6$ cells/ml.

100 µg portions of plasmid DNA were placed in sterile electroporation cuvetres (electrode spacing 0.4 cm), and 400 µl of cell suspension were added to each cuvette and thoroughly mixed. This mixture was preincubated on ice for 10 min. The electroporation took place at 200 volt and 960 µF with time constants of 40–60 ms (Gene Pulser™, BioRAD, Munich). After incubation at room temperature for 10 minutes, the cells were suspended in 21 ml of OptiMEM medium (*Gibco BRL Life Technologies GmbH, Dieselstr.* 5, 76344 Eggenstein) with 10% fetal calf serum and penicillin/streptomycin (100 iu), and 200 µl of cell suspension were pipetted into each of the wells of a 96-well microtitre plate.

The cells were incubated for 24 h after electroporation. The OptiMEM medium with 10% fetal calf serum and penicllin/streptomycin (100 iu) was then replaced by OptiMEM medium with 0.5% fetal calf serum and penicillin/streptomycin (100 iu). The compounds to be tested had previously been taken up in the latter in the respective concentrations. In addition IL-6 (final concentration: 10 ng/ml) was added as inducer to each mixture. Stimulated and nonstimulated mixtures were used as controls.

Cytotoxic effects of the compounds on the cells were investigated by microscopy after 24 h. Likewise after 24 h. the SEAP activity was determined using the Phospha-Light™ chemoluminescence assay (Perkins-Elmer Applied Biosystems, Langen) and, under the chosen conditions, is directly proportional to the SEAP concentration in the analysed sample. The chemoluminescence was measured in 96-well microtitre plates using a luminometer (Labsystems Luminoskan RT from Labsystem, Frankfurt/M).

For example, after induction with IL-6, the concentration for half-maximal SEAP synthesis inhibition ($IC_{50}$) of the compound of the formula (I) (*galiella lactone*) is 50–100 nM. This compound thus represents a potent inhibitor of IL-6-induced and Stat3-mediated SEAP synthesis.

Example B

Effect on tyrosine-705 and serine-727 phosphorylation of Stat3 and on tyrosine-701 phosphorylation of Stat1.

A crucial step in IL-6-dependent intracellular signal transduction is the phosphorylation of tyrosine-705 in Stat3 and tyrosine-701 in Stat1. Prevention of this phosphorylation interrupts the IL-6-dependent signal cascade, and the otherwise observable IL-6-induced expression of the target genes does not occur. However, inhibitors which inhibit the Stat3 and Stat1 phosphorylation also have crucial effects on other signal cascades, and therefore pharmaceutically usable inhibitors of IL-6-dependent gene expression should, in the concentration range in which they display their pharmacological effect, affect the Stat3 or Stat1 phosphorylation only slightly or not at all.

For this reason, for further demonstration of the inhibition of IL-6-induced phosphorylation of Stat3 and Stat1, the following bioassay was carried out.

The procedure for this demonstration is described below:

Seed out HepG2 cells in Petri dishes (diameter: 10 cm) (OptiMEM medium with 10% fetal calf serum and penicillin/streptomycin (100 iu) cell density: $5 \times 10^5$ cell/ml). Incubate in a moist atmosphere with 5% $CO_2$ at 37° C. for 24 h. Replace medium by fresh OptiMEM medium with 0.5% fetal calf serum and penicillin/streptomycin (100 iu) and incubate for a further 48 h. Replace medium by fresh OptiMEM medium with 0.5% fetal calf serum and penicillin/streptomycin (100 iu), add test substances in various concentrations, and incubate for 60 min. 5 µl of the substances dissolved in ethanol, or only ethanol (controls), were added per mixture (10 ml). Induce cells by adding IL-6 (final concentrations 50 ng/ml).

After 20 min. remove medium and wash cell lawn twice wtih 1.5 ml of ice-cold PBS (137 mM NaCl, 2.7 mM KCl, 8.1 mM $Na_2HPO_4 \times 2H_2O$, 1.5 mM $KH_2PO_4$) each time. Add 1.5 ml of extraction buffer (1% Trition X-100, 50 mM Tris-HCl, 10 mM EDTA, 2 mM EGTA, 500 mM NaCl, 10 mM NaF, 1 mM $Na_3VO_4$, 1:50 complete protease inhibitor cocktail (Roche Diagnostics GmbH, Roche Molecular Biochemicals, Sandhofer Str. 116, 68305 Mannheim Germany), pH 7.5) and scrape off cells with a cell scraper and transfer them into a 10 m centrifuge tube. Wash Petri dish with 1.5 ml of extraction buffer, and combine the resulting suspension with that from point 7. Pellet suspension at 4° C. for 30 min (3 000×g). Transfer supernatant into a new centrifuge tube. Add 90 µl of protein A-Sepharose (50:50 in PBS) and rotate end over end at 4° C. for 2 h. Pellet suspension at 4° C. for 5 min (3 000×g). Transfer supernatant into a new centrifuge tube. Add 5 µl of Stat3 antibody and rotate in end over end at 4° C. overnight. Add 90 µl of protein A-Sepharose (50:50 in PBS) and rotate end over end at 4° C. for 2 h. Pellet suspension at 4° C. for 5 min (3 000×g). Discard supernatant. Wash pellet twice with washing buffer 1 (10 mM Tris-HCl, 2 mM EDTA, 100 mM NaCl, 0.2% NP-40, pH 7.5), once with washing buffer 2 (10 mM Tri-HC1, 2 mM EDTA, 500 mM NaCl, 0.2% NP-40, pH 7.5) and once with washing buffer 3 (10 mM Tris-HCl, pH 7.5) Pellet suspension at 4° C. for 10 min (3 000×g) and carefully remove supernatant. After addition of 80 µl of washing buffer 3 and 40 µl of SDS gel buffer (50 mJ Tri-HCl, 100 mM dithiothreitol, 2% SDS, 0.1% bromophenol blue, 10% glycerol) to the pellet, the latter is boiled in a water bath for 5 min. Pellet suspension at 4° C. for 1 min (10 000×g).

20 µl of supernatant are fractionated by electrophoresis on a 6.5% SDS polyacrylamide gel with a 5% stacking gel (16×18 cm) (7° C. 10 V/cm, 25 mM Tris, 250 mM glycine, 0.1% SDS, pH 8.3). After the end of the electrophoresis, the gels were equiliberated in electrotrans buffer (25 mM Tris, 192 mM glycine, 20% methanol, pH 8.3). The proteins were then transferred using an electroblotter (Trans-Blot SD, BioRad, Munich) at 25 V onto a fabric-reinforced nitrocellulose membrane (Optitran, Schliecher & Schull, Dassel).

Before applying the respective antibodies, the membranes were incubated in blocking buffer 1 (25 mM Tri-HCl, 137 mM NaCl, 2.7 mM KCl, 5% (w/v) skimmed milk powder, 0.1% Tween 20) at 4° C. overnight. Primary phospho-Stat3 antibodies were diluted 1:2 500 in blocking buffer II (250 mM Tris-HCl, 137 mM NaCl, 2.7 mM KCl, 5% (w/v) bovine serum albumin, 0.1% Tween 20) and incubated with the membrane at 4° C. overnight. The procedure with the secondary antibodies was analogous but with use of blocking buffer I in this case. Between the antibody applications, washing was carried out with washing buffer (25 mM Tris-HCl, 137 mM NaCl, 2.7 mM KCl, 0.1% Tween 20) for 20 min several times. The secondary antibodies chosen for visualizing the proteins were conjugates with horseradish peroxidase. Detection takes place in this case by chemoluminescence in accordance with the manufacturer's information (New England Biolabs, Beverly, USA).

The compound of the formula (I) (*galiella lactone*) had no effect on the phosphorylation of Stat3 or Stat1 at any of the concentrations tested (up to 16 µg/ml, equivalent to 165 µM).

Figure 3:
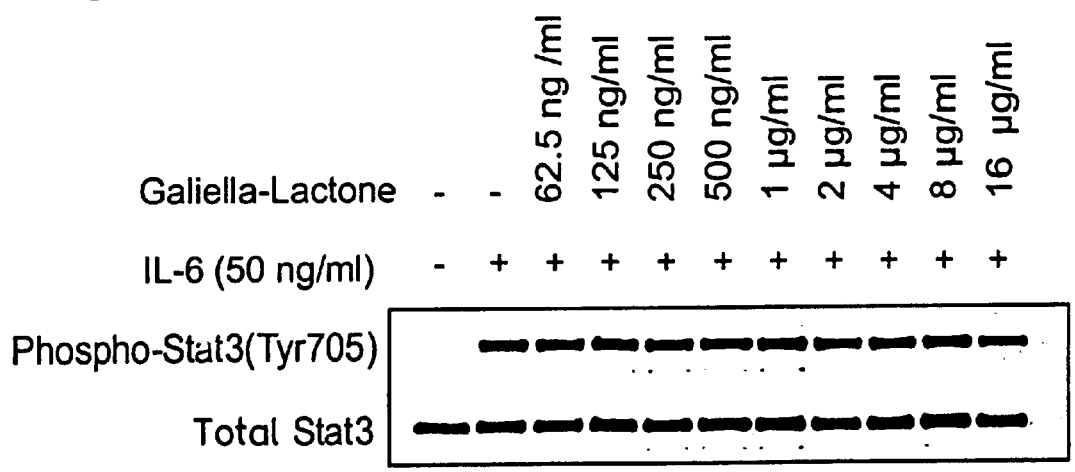

FIG. 3 depicts the effect of *galiella lactone* or tyrosine phosphorylation of Stat3. The tyrosine phosphorylation was detected using a phospho-Stat3 (Tyr705) antibody (top row). The same blot was stripped and treated with a Stat3 antibody (lower row).

Figure 4:
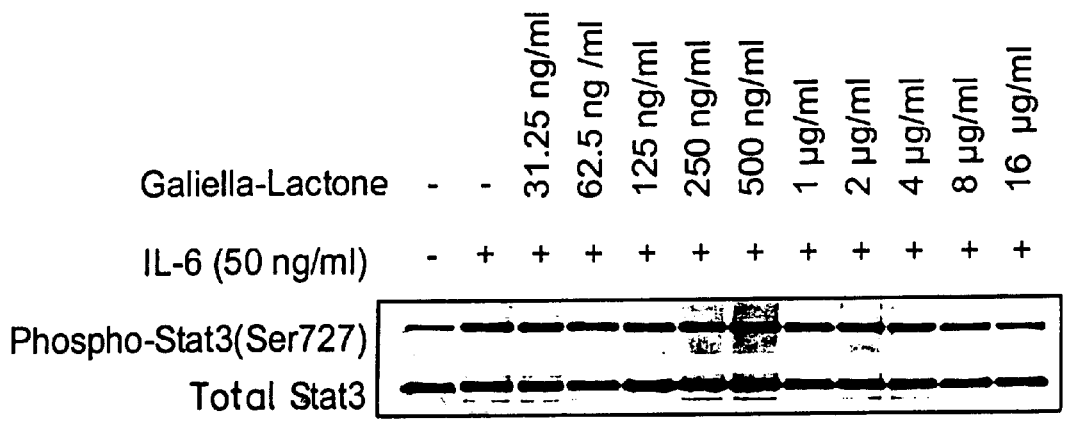

FIG. 4 depicts the effect of *galiella lactone* on the serine phosphorylation of Stat3. The serine phosphorylation was detected using a phospho-Stat3 (Ser727) antibody (top row). The same blot was stripped and treated with a Stat3 antibody (lower row).

Figure 5:
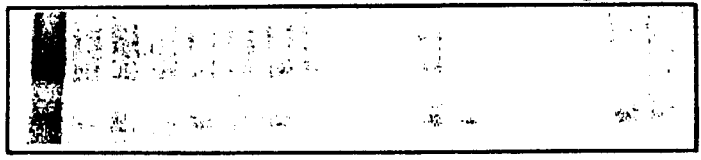

FIG. 5 depicts the effect of *galiella lactone* on tyrosine phosphorylation of Stat1. The tyrosine phosphorylation was detected using a phospho-Stat1 (Tyr701) antibody (top row). The same block was stripped and treated with a Stat1 antibody (lower row).

Example C

Effect on the DNA binding of activated, i.e. tyrosine 705-phosphorylated, Stat3 dimers The DNA binding of activated Stat3 dimers to their binding sites in the promoters of the target genes is the basic requirement for transcriptional activation of these genes. At the same time, this step is specific for Stat3, i.e. inhibition of this step would result in specific inhibition of IL-6-induced and Stat3-mediated expression of the target genes without simultaneously affecting other signal cascades. The effect of the various compounds on the DNA binding ability of the phosphorylated and thus activated Stat3 dimers was analysed by carrying out electrophoretic mobility shift assays (EMSAs, gel shift assays).

Assay procedure

The procedure was as described in *Nature*, 1993, 362: 79–83 and *Mol. Cell Biol*, 1998, 18: 2108–17. The DNA probe used was the $^{32}$P-labelled, double-stranded oligonucleotide with the m67SIE recognition sequence (S2) (wild-type) (cf. *EMBO J.* 1995, 14: 1421–9)

5'-GATCCATTTCCCGTAAATC-3' SEQ ID NO:3
3'-CTAGGTAAAGGGCATTTAG-5' SEQ ID NO:4

The compound of the formula (I) (*galiella lactone*) for example even at a concentration of 16 ng/ml (82 nM) completely inhibits the binding of the activated Stat3 dimers to their recognition sequence. It was possible to show with control mixtures in which the induced control was preincubated with phospho-Stat3 (tyrosine 705)-specific antibodies that it is Stat3 phosphorylated on the tyrosine 705 residue which binds to the m67SIE probe (see FIG. 6).

Figure 6:
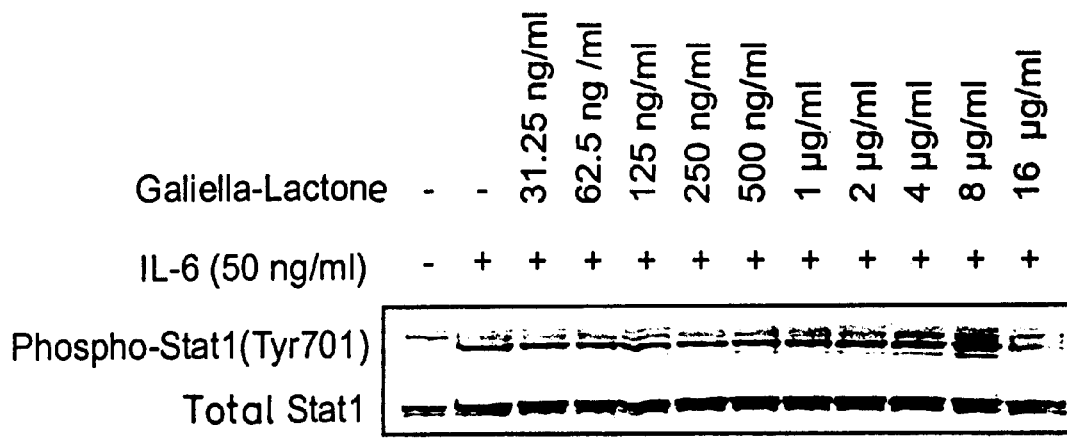

The meanings in FIG. 6 are:

Comp (100 x): control mixture to which a 100-fold excess of the unlabelled probe was added.

o.P.: mixture to which no cell extract was added.

p-Stat3-Ab: mixture to which 1 µg of a phospho-Stat3 (tyrosine 705)-specific antibody was added.

Stat3-Ab: mixture to which 1 µg of Stat3 antibody was added.

Example D

Inhibition of the N-methyl-D-aspartate-mediated calcium influx into primary neurons of the central nervous system after chronic interleukin-6 treatment Cultures of primary neurons were obtained from the cerebella of rats 6 to 8 days old as described by B. Engelsen and R. Bjerkvig [in R. I. Freshney (Editor) *Culture of Animal Cells*, 2nd Edition, Alan R. Liss, Inc. New York 1987, 277–279]. After removal of the tissue, single cells were obtained using papain and were seeded out in a density of 200 00 cells per well in microtitre plates (96 wells) coated with poly-D-lysine. The cells were cultivated in a growth medium consisting of DMEM/F12, 10% heat-inactivated horse serum. 25 mM KCl, 30 mM glucose, 2 mM glutamine. In order to minimize the number of glial cells, 5-fluoro-2'-deoxyuridine (20 µg/ml) was added on the first and fourth day in culture. The cultures obtained in this way consisted of more than 95% neurons.

Human recombinant interluekin-6 (IL-6) was dissolved in physiological salt solution (Hank's balanced salt solution) and added to neuron cultures on days, 1, 4, 7 and 11 after the start of culturing (final) concentration 5 ng/ml). 10 minutes before each IL-6 addition the cells were treated with *galiella lactone* (final concentration 1 µM).

12 days after the start of culturing, the N-methyl-D-asparate (NMDA)-induced changes in the intracellular calcium level were measured using a fluorescence plate reader (Ascent Fluoroscan). For this, the cells were loaded with Fluo-3 acetomethyl ester 5.5 µM in the presence of 0.003% pluronic acid in physiological salt solution at 37° C. for 60 minutes. The incubation medium was then removed and replaced by fresh salt solution. The cells were stimulated by adding NMDA (final concentration 200 µM) in the presence of glycine (final concentration 5 µM), and the fluroescence was measured at 15-second intervals over a period of one minute (excitation 485 nm. emission 530 nm). Intracellular calcium concentrations were calculated by the formula $[Ca^2]_i = K_d \cdot (F - F_{min})/(F_{max} \cdot F)$, where $K_d$ represents the dissociation constant for Fluo-3 at room temperature (450 mM), F represents the measured fluorescence, $F_{max}$ represents the maximum fluorescence as determined by the addition of 20 µM ionomycin, and $F_{min}$ represents the minimum fluorescence as measured on cells not labeled with Fluo-3.

The arithmetic means was formed from the intracellular calcium concentrations found at all four times of measurement, and the percentage change from the unstimulated controls (basa) calcium concentration) was calculated.

Figure 7:
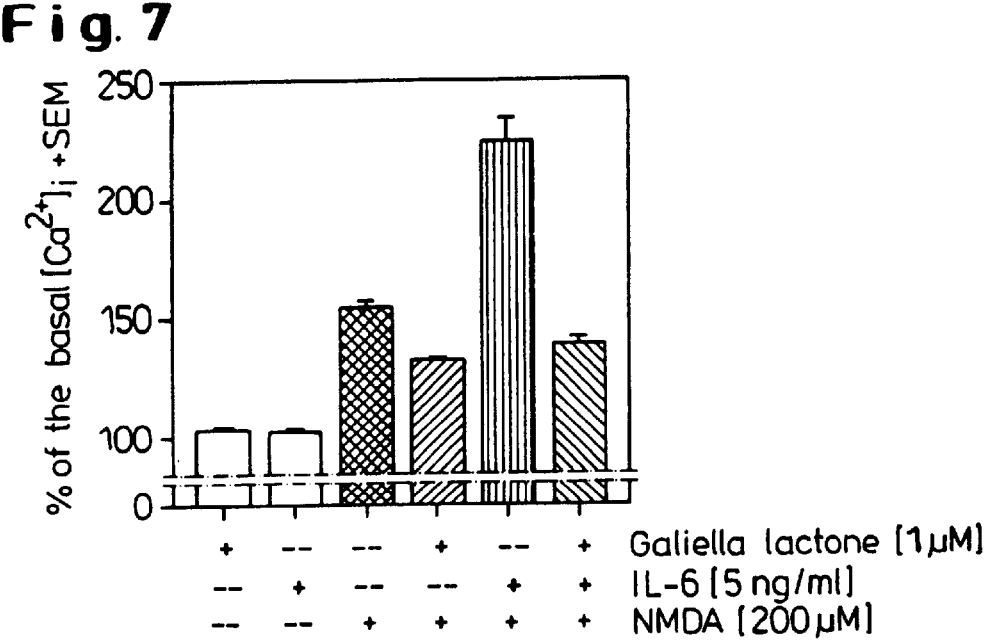

Chronic treatment of primary neurons of the rat cerebellum with *galiella lactone* or IL-6 had no effect on the basal calcium level (FIG. 7, first and second bar from the left). Addition of NMDA caused an increase in the average intracellular calcium concentration during the one-minute measurement period to about 150% of the basal level and was somewhat reduced after chronic administration of *galiella lactone* (FIG. 7, third and fourth bar from the left). Compared with untreated cultures, the NMDA-mediated intracellular calcium response was significantly potentiated in cultures chronically treated with IL-6 (FIG. 7, second bar from the right). Addition of *galiella lactone* completely prevented the IL-6-induced enhancement of the NMDA-mediated calcium influx (FIG. 7, first bar from the right).

Example E

6-Hydroxydopamine (6-OH-DA) lesion in the rat

Degeneration of dopaminergic nigrostriatal and striatopallidal neurotransmission represents the main characteristic of Parkinson's disease. The clinical picture of Parkinson's disease can to a large extent be simulated in an animal model in which rats receive intracerebral injection of the neurotoxin 6-hydroxydopamine (6OH-DA).

For the experiments described, male rats (Harlan Winkelmann, Germany: weight at start of experiment: 200 to 250 g) were used. The experimental were housed under control conditions (humidity, temperature) and with a 12-hour light/dark cycle.

The animal had free access to water and food when they were not undergoing an experiment. The experimental procedure described below was approved and monitored by the relevant government authorities.

The animals received, on the day of operation, 30 minutes before the lesion, pargyline (Sigma, St. Louis, Mo., USA; 50 mg/kg i.p.) and desmethylimipramine HCl (Sigma: 25 mg/kg i.p.) respectively in order to suppress metabolism of 6-hydroxydopamine and in order to prevent uptake of 6-hydroxydopamine into noradrenegic structures. After induction of anaesthesia with sodium pentobarbital (50 mg/kg), the experimental animals were fixed in a sterotactic frame. The ingrostriatal neurotransmission lesion was brought about by a single unilateral injection of 8 µg of 6-OH-DA HBr (Sigma, St. Louis, Mo., USA), dissolved in 4 µl of a 0.01% strength ascorbic acid/saline solution. The solution was injected slowly at 1 µl/min. The Konig and Klippel injection coordinates are: 2.4 mm anterial, 1.49 mm lateral, −2.7 mm ventral. After the injection, the injection needle was left in situ for 5 minutes in order to facilitate diffusion of the neurotoxin.

After the operation, the animals were placed on a warm plate and, after awakening while being monitored, returned to their cages and received food and water ad libitum.

The behaviour testing took place after development of the maximum damage, 3 weeks after the injection of neurotoxin. In the active substance group, the animals were treated with the substance from one day after the operation until the end of the experiment 28 days after the operation.

Figure 8:
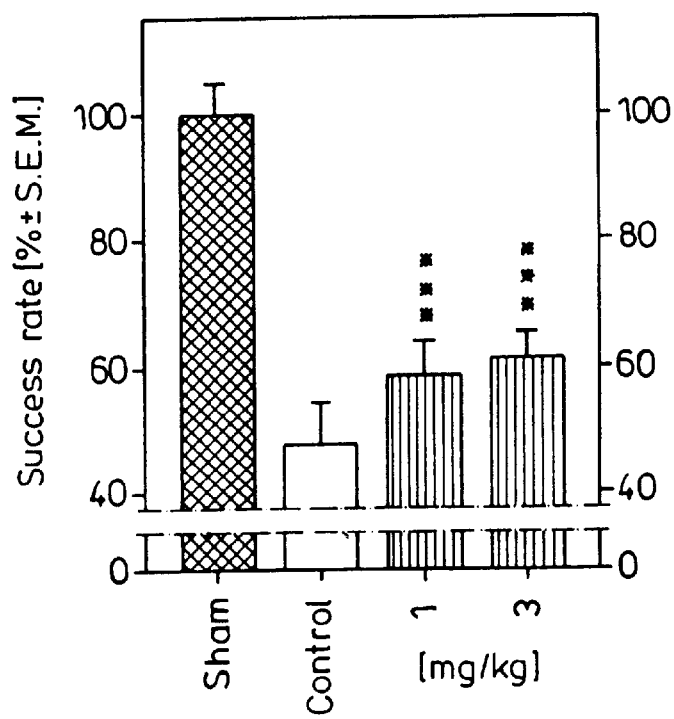

The motor deficits after the lesion were quantified by the staircase test (forepaw coordination test) as described in the literature (*Neuroscience* 1995, 67: 837–848) and are depicted in FIG. 8. *Galiella lactone* improved the fine motor control of the forepaws after dosages of 1.0 and 3.0 mg/kg, bid, i.p. (FIG. 8, the two bars marked with "****")

Example F

Growth inhibition test to determine the cytotoxic properties on tumour cell lines The human colon cell lines SW 480 and HT 29 (ATCC Nos. CCL 228 and HBT-38), the mouse melanoma cell line B16F10 and the human prostate tumour cell lines LNCaP-FGC, PC-3 and DU 145 (ATCC No. CRL-10995, CRL-1435, HTB-81) were grown in RPMI 1640 medium with addition of 10% FCS in Roux dishes. This was followed by trypsinization and taking up in RPMI plus 10% FCS to a cell count of 50 000 cell/ml. 100 µl of cell suspension/well were put in a 96-microwell plate and incubated in a $CO_2$ incubator at 37° C. for 1 day. A further 100 µl of RPMI medium and 1 µl of DMSO with *galiella lactone* were then added. The growth was monitored after day 6. For this purpose, 40 µl of MTT solution (3-(4,5-dimethylthiazol-2-yl)-2,5-diphenyltetrazolium bromide) with an initial concentration of 5 mg/ml of $H_2O$ were added to each microwell. Incubation took place in a $CO_2$ incubator at 37° C. for 5 hours. The medium was then separated off, and 100 µl of i-propanol/well were added. After shaking with 100 µl of $H_2O$ for 30 min, the extinction at 540 nm was measured with a Titertek Multiscan MCC/340 (flow).

The cytotoxic effect is indicated in the table as $IC_{50}$ (*galiella lactone* concentration in µM) for the various tumour cell lines:

| Cell line | SW480 | HAT29 | B16F10 | LNCaP | PC-3 | DU145 |
|---|---|---|---|---|---|---|
| $IC_{50}$ | 5 | 5 | 3 | 2 | 4 | 4.5 |

BRIEF DESCRIPTIONS OF THE FIGURES

FIG 1:

Vector map of the initial vector pTK/SEAP with the cleavage sites for the restriction enzymes used, and a selection of unique cleavage sites. Also shown are the gene of secreted alkaline phosphatase (SEAP), the thymidine kinase promoter (TKPro), the mRNA polyadenylation signal of the SV40 virus (SV40 poly (A)), the origin of replication from the pUC plasmid family (ori), the multiple cloning site (MCS) and the single-strand origin of replication of phage F1 (f1).

FIG. 2:

Vector map of pMW-IRF7 with a selection of unique cleavage sites.

FIG. 3:

Effect of *galiella lactone* on the tyrosine phosphorylation of Stat3. The tyrosine phosphorylation was detected using a phospho-Stat3(Tyr705) antibody (top row). The same blot was stripped and treated with a Stat3 antibody (lower row).

FIG. 4:

Effect of *galiella lactone* on the serine phosphorylation of Stat3. The serine phosphorylation was detected using a phospho-Stat3(Ser727) antibody (top row). The same blot was stripped and treated with a Stat3 antibody (lower row).

FIG. 5:

Effect of *galiella lactone* on the tyrosine phosphorylation of Stat1. The tyrosine phosphorylation was detected using a phospho-Stat1 (Tyr701) antibody (top row). The same blot was stripped and treated with a Stat1 antibody (lower row).

FIG. 6:

Effect of *galiella lactone* on the binding of activated Stat3 dimers to their DNA recognition sequence. Probe used: m67SIE, induction time 20 minutes: cell line: HepG2.

FIG. 7:

Inhibition of the potentiation, induced chronic IL-6 administration, of the NMDA-mediated calcium influx into primary neurons of the rat cerebellum by *galiella lactone*. Cerebellar neurons cultivated in the presence of IL-6 were treated with *galiella lactone*, and the NMDA-induced change in the intracellular calcium concentration ($[Ca^{2+}]_i$) was determined by fluorimetry. The average calcium concentration during the one-minute measurement period was calculated and expressed as a per cent of the basal intracellular calcium concentration. The data are derived from a representative experiment which was carried out in 6-fold replicates. A "+" under a bar means that the neurons were treated with the substance indicated on the right in each case; "−" means that they were not treated therewith SEM= standard error of the mean.

FIG. 8:

*Galiella lactone* significantly improves the fine motor control of the forepaws 4 weeks after unilateral 6-hydroxydopamine lesion of the *substantia nigra*. *Galiella lactone* was administered intraperitoneally (i.p.) twice a day (bid) (in dosages of 1, 3 and 10 mg/kg), starting with day 1 after the operation, and the fine motor control was quantified in the staircase test. The average success rate of the sham-operated animals (sham group; animals who underwent the appropriate surgical interventions but no 6-hydroxydopamine was administered) in collecting the offered pieces of food was set equal to 100%, and all other values were calculated correspondingly. The data are derived from an experiment with n=12 animals/group. SEM=standard error of the mean:

\*\*\*: statistically significant with a probability of error of less than 0.1% (p<0.001).

What is claimed is:

1. Pharmaceutical containing *Galiella lactone* and a pharmaceutically acceptable excipient.

2. A method of treating or preventing fibrotic disorders of the liver or other organs, cerebrovascular disorder, autoimmune diseases affecting the CNS or PNS, chronic neurodegenerative disorders, psychological disorders, peripheral neuropathies, pain, cardiovascular disorder, inflammatory diseases of the gastrointestinal tract, amyloidoses, and tumours, comprising administering to a mammal an effective amount of a *galiella lactone*.

3. The method of claim 1, wherein said *galiella lactone* has the following $^1$H-NMR data (500 MHz, δ/ppm, CDCl$_3$): 6.85 (d); 2.53 (m); 0.90 (m); 2.13 (m); 1.02 (m); 1.71 (m); 1.60 (m); 1.95 (m); 4.64 (m); 1.05 (m).

4. The method of claim 1, wherein said *galiella lactone* has the following $^{13}$C-NMR data (125 MHz; δ/ppm, CDCl$_3$); 170.4; 130.6; 149.6; 28.6; 32.7; 42.7; 31.0; 31.0; 90.0; 81.3; 20.5.

5. The method of claim 1, wherein said *galiella lactone* has the following characteristic peaks in the IR spectrum: 3435 cm$^{-1}$, 2961 to 2933 cm$^{-1}$, 1742 cm$^{-1}$, 1670 cm$^{-1}$, 1460 cm$^{-1}$.

* * * * *

UNITED STATES PATENT AND TRADEMARK OFFICE
CERTIFICATE OF CORRECTION

PATENT NO.    : 6,512,007 B1
DATED         : January 28, 2003
INVENTOR(S)   : Jorg Baumgarten et al.

It is certified that error appears in the above-identified patent and that said Letters Patent is hereby corrected as shown below:

Column 15,
Line 38, please delete "claim 1" and insert -- claim 2 --.

Column 16,
Lines 29 and 33, please delete "claim 1" and insert -- claim 2 --.
Line 35, please delete "$cm^{-1}$'2961" and insert -- $cm^{-1}$, 2961 --.

Signed and Sealed this

Seventeenth Day of June, 2003

JAMES E. ROGAN
*Director of the United States Patent and Trademark Office*